US012642489B2

(12) United States Patent
Siegel et al.

(10) Patent No.: US 12,642,489 B2
(45) Date of Patent: Jun. 2, 2026

(54) PATIENT BED TRACKING FOR MEDICAL IMAGING SYSTEM

(71) Applicant: Siemens Medical Solutions USA, Inc., Malvern, PA (US)

(72) Inventors: Stefan B. Siegel, Knoxville, TN (US); Ziad Burbar, Knoxville, TN (US); Inki Hong, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1422 days.

(21) Appl. No.: 17/248,180

(22) Filed: Jan. 13, 2021

(65) Prior Publication Data

US 2021/0228175 A1      Jul. 29, 2021

Related U.S. Application Data

(60) Provisional application No. 62/964,685, filed on Jan. 23, 2020.

(51) Int. Cl.
| | |
|---|---|
| *A61B 5/00* | (2006.01) |
| *A61B 6/00* | (2024.01) |
| *A61B 6/03* | (2006.01) |
| *A61B 6/04* | (2006.01) |

(52) U.S. Cl.
CPC .............. *A61B 5/704* (2013.01); *A61B 6/032* (2013.01); *A61B 6/037* (2013.01); *A61B*

*6/0407* (2013.01); *A61B 6/547* (2013.01); *A61B 6/4417* (2013.01); *A61B 2562/0219* (2013.01)

(58) Field of Classification Search
CPC ..... A61B 5/704; A61B 6/0442; A61B 6/0471; A61B 6/00; A61B 6/0407; A61B 5/70; A61B 6/032; A61B 6/037; A61B 6/42; A61B 6/4266; A61B 6/547; A61B 6/4417; A61B 2562/0219
See application file for complete search history.

(56) References Cited

U.S. PATENT DOCUMENTS

| | | | | |
|---|---|---|---|---|
| 9,297,913 | B2 * | 3/2016 | Grobshtein | G06T 11/005 |
| 2010/0034435 | A1 * | 2/2010 | Kariv | A61B 6/5276 5/601 |
| 2014/0275998 | A1 * | 9/2014 | Eichler | A61B 6/547 600/424 |
| 2020/0077970 | A1 * | 3/2020 | Judkins | A61B 6/547 |

* cited by examiner

*Primary Examiner* — David R Hare
*Assistant Examiner* — Deborah Talitha Gedeon

(57) ABSTRACT

Provided is a medical imaging scanner system such as a PET scanner system having a patient bed pallet that is provided with at least one multi-axis motion sensor for monitoring the movement of the patient bed pallet and detecting any deviation in the orientation of the patient bed pallet from a predetermined desired orientation during the movement.

12 Claims, 4 Drawing Sheets

PATIENT BED TRACKING FOR MEDICAL IMAGING SYSTEM

CROSS-REFERENCE TO RELATED APPLICATIONS

The present patent document claims the benefit of the filing date under 35 U.S.C. § 119(e) of Provisional U.S. Patent Application Ser. No. 62/964,685, filed Jan. 23, 2020, which is hereby incorporated by reference.

FIELD

The present disclosure generally relates to medical imaging systems that utilize a movable patient bed.

BACKGROUND

During a medical image scanning operation in such systems as MRI, CT, SPECT, PET, SPECT/CT, and PET/CT scanners, a patient may be moved through the scanner's field of view (FOV) generally in a step and shoot (S & S) mode, or a continuous bed motion (CBM) mode to scan different regions of the patient. In these scanning modes, the orientation of the patient in the scanner's FOV needs to be where intended in order to produce accurate scan images.

A single bed position acquisition may not match the orientation in a complementary modality such as CT or MRI, and the orientation may change at the fixed steps during S & S mode acquisition. A mismatch in the patient positioning between PET and the complementary modalities, such as CT or MRI, can introduce artifacts in the PET images should corrections in the PET image processing be based on the data from these other modalities. These modalities are often used for attenuation correction, for example, and in the conventional systems the error (artifact) could be introduced before the patient bed positioning error is detected. This is not desired because a severe artifact could be misconstrued as a pathology. Similar concerns exist in SPECT/CT scanners.

In CBM PET scanners, for example, the patient is moved through the scanner's FOV in a continuous mode. The patient lies on a patient bed which is attached to a moving pallet that moves the patient bed through the FOV of the scanner.

Over the course of the movement of the patient bed in continuous bed motion (CBM) PET scanning, the pallet orientation can vary with axial location. This effect can be introduced by structural imperfection in the floor. This imperfection can appear over time, post-installation, due to settling of the floor structure or heavy machinery installed in the facilities.

Generally, this issue has been ignored until the PET scan image quality degrades to a noticeable level. Then, PET scanner patient bed assembly is re-leveled. Thus, an improvement to the PET scanners in the ability to monitor the positional errors in the patient bed is desired.

SUMMARY

Provided is a system for tracking the imperfect orientation of the patient bed pallet orientation by providing a multi-axis motion sensor on the tip of the pallet. This can track and measure a small angular deviation of the patient bed pallet due to the long moment of the patient bed.

According to some embodiments, a medical image scanner is disclosed. The medical image scanner comprises: a detector ring having a patient tunnel; a patient bed pallet that is configured to move in a path within the patient tunnel; and at least one multi-axis motion sensor provided on the patient bed pallet, wherein the multi-axis motion sensor monitors the movement of the patient bed pallet when the patient bed pellet is moving in the path within the patient tunnel and detects any deviation in the patient bed pallet's orientation from a predetermined desired orientation at any selected location along the path.

According to some embodiments, a patient bed pallet for a medical image scanner system is disclosed. The patient bed pallet comprises: at least one multi-axis motion sensor provided on the patient bed pallet, wherein the patient bed pallet is configured to move in a predetermined path, wherein the multi-axis motion sensor monitors the movement of the patient bed pallet when the patient bed pellet is moving in the predetermined path and detects any deviation in the patient bed pallet's orientation from a predetermined desired orientation at any selected location along the predetermined path.

BRIEF DESCRIPTION OF THE DRAWINGS

The features of the embodiments described herein will be more fully disclosed in the following detailed description, which is to be considered together with the accompanying drawings wherein like numbers refer to like parts. All drawing figures are schematic and they are not intended to represent actual dimensions of the structures or relative ratios of their dimensions.

DETAILED DESCRIPTION

Figure 1:
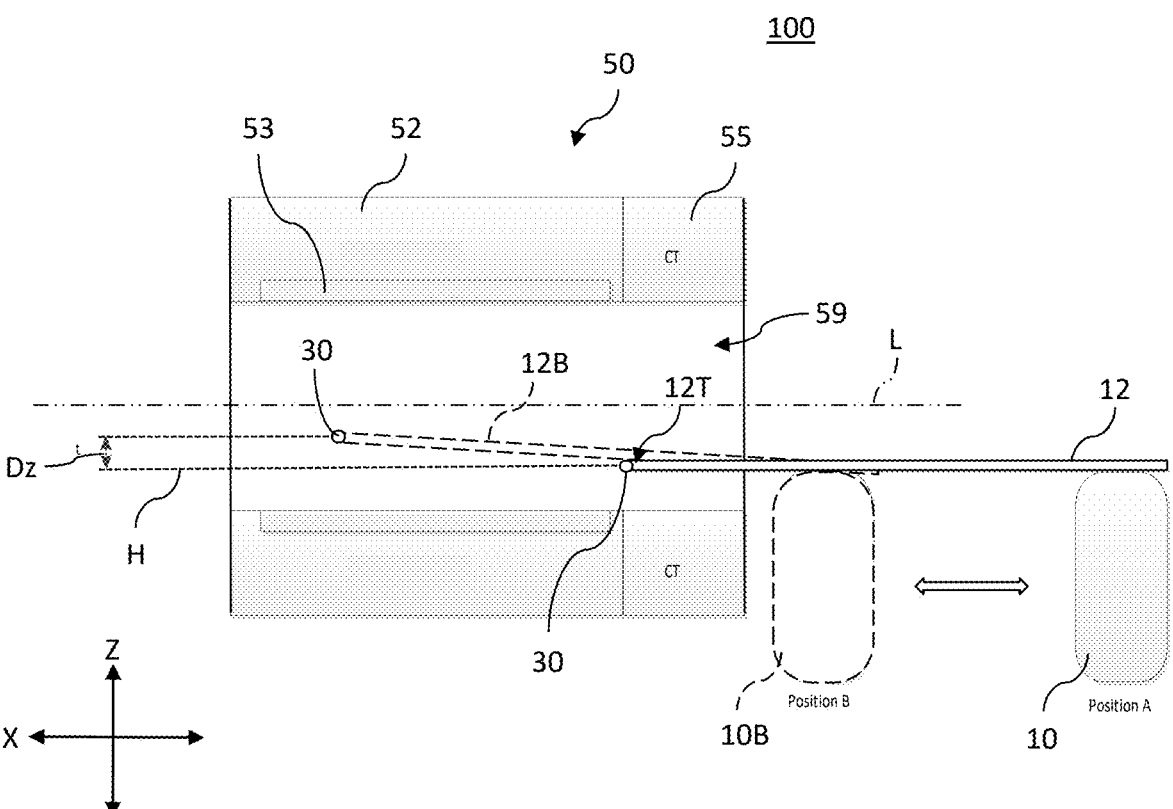
FIG. 1 is an illustration showing a side view of a patient bed movement within the axial field of view of a scanner between position A and position B.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

Disclosed herein is a system for tracking the motion of a patient bed pallet in a medical imaging system and detect any deviation from the intended path for the patient bed pallet within the medical imaging system's axial FOV. By detecting the deviation of the patient bed pallet, one can determine when a physical adjustment or correction of the patient bed pallet may be required.

FIG. 1 is an illustration showing a side view of a gantry portion of an example of a PET/CT scanner system 100. The detector ring 50 is shown in cross-section so that the patient bed pallet 12 can be shown. The detector ring 50 comprises an array of PET detectors 53 that define the axial FOV of the PET modality 52, a CT modality 55, and a patient tunnel 59 defined by the bore of the detector ring 50. The longitudinal axis of the detector ring 50 is identified by the line L.

The patient bed pallet 12 is supported on a base 10. The patient bed pallet 12 and the base 10 are configured to be movable between Position A and Position B. At Position A, the patient bed pallet 12 is near the beginning of the axial FOV of the PET detectors 53. At Position B, the patient bed pallet 12 is advanced further into the axial FOV of the PET detectors. In FIG. 1, the position of the patient bed pallet and the base at Position B are represented by the broken line rendering 12B and 10B, respectively. The movement from Position A to Position represents the movement of a patient during an imaging scan whether it is a S & S mode or a CBM mode.

Figure 4:
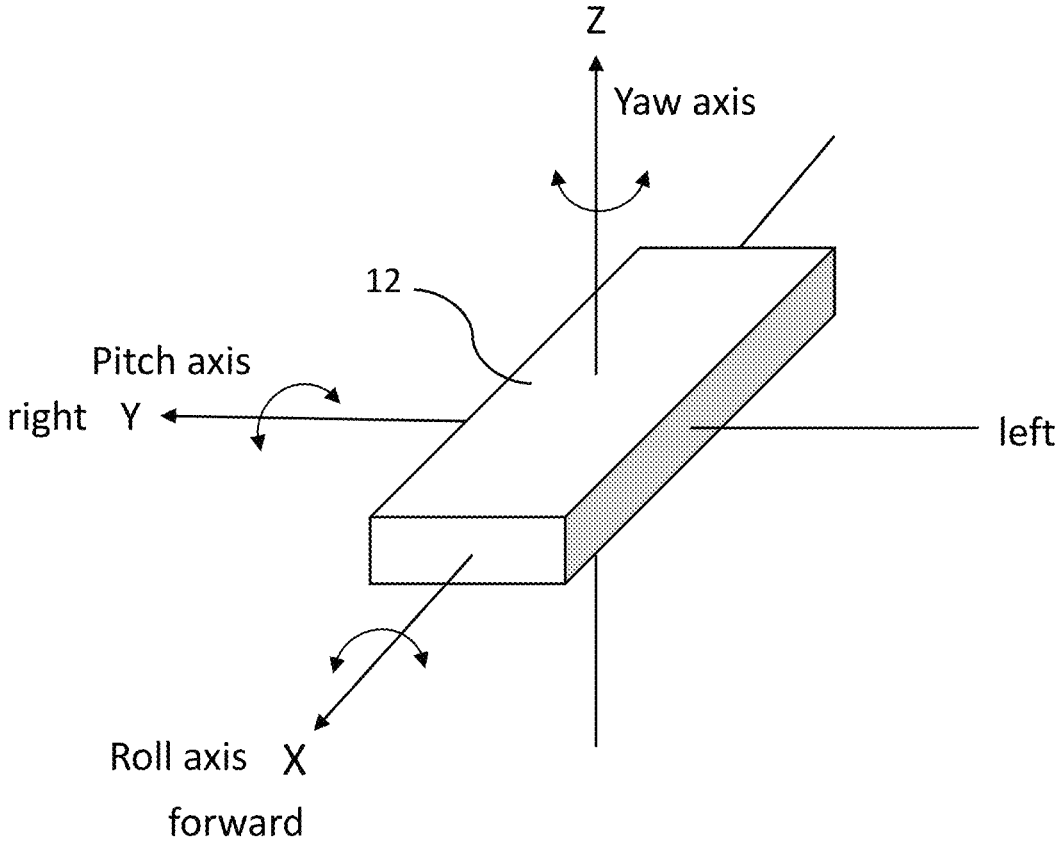
FIG. 4 is an illustration showing the three primary axes X, Y, and Z of a patient bed pallet defined for the purpose of describing the roll, pitch, and yaw motions of the patient bed pallet.

Referring to FIG. 4, the linear motion of the patient bed pallet 12 is defined using the roll, pitch, and yaw descriptives typically used in linear systems. The associated three primary axes are X, Y, and Z. The two axes of the horizontal plane are defined as X and Y, with the X axis being in the direction of motion of the patient bed pallet 12. The Y axis is orthogonal to the direction of motion and is also in the horizontal plane. The Z axis is orthogonal to both the X and Y axes, but it is located in the vertical plane. A motion of the pallet 12 that results in a rotation in the orientation of the pallet 12 about the X axis is a roll. A motion of the pallet 12 that results in a rotation in the orientation of the pallet 12 about the Y axis is pitch. A motion of the pallet 12 that results in a rotation in the orientation of the pallet 12 about the Z axis is yaw.

Ideally, medical imaging systems such as the PET/CT scanner system 100 shown in FIG. 1 are set up so that the movement of the patient bed pallet 12 is maintained parallel to the longitudinal axis L of the detector ring 50 in the plane of the patient bed pallet 12. This means that the patient bed pallet 12 should remain parallel to the longitudinal axis L in the 3-D space throughout its movement from Point A to Point B without any roll, pitch, or yaw. Thus, when viewed from the side as in FIG. 1, the patient bed pallet 12 should remain parallel to the longitudinal axis L throughout its movement from Point A to Point B without any pitch or roll. Also, when viewed from the top as shown in FIG. 2, the patient bed pallet 12 should remain parallel to the longitudinal axis L direction throughout its movement from Point A to Point B without any yaw within the axial field of view of a scanner between position A and position B.

In the example shown in FIG. 1, line H is a line that is parallel to the longitudinal axis L and represents the position of the patient bed pallet 12 when in Position A. As can be seen, when the patient bed pallet 12 has advanced to Position B as represented by the dashed outline 12B, the patient bed pallet 12 has pitched upward and the leading tip of the patient bed pallet has deviated from the line H by a displacement Dz.

Figure 2:
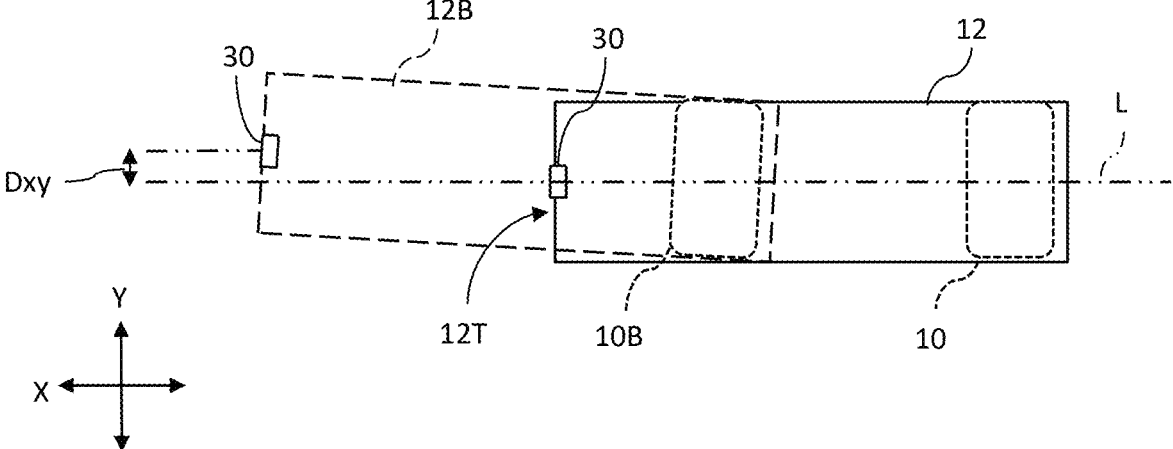
FIG. 2 is an illustration showing a top view of a patient bed movement within the axial field of view of a scanner between position A and position B.

In another example shown in FIG. 2, which is a top view of the patient bed pallet 12 of FIG. 1, the patient bed pallet 12 has yawed in the clockwise direction as the patient bed pallet 12 advanced to Position B from Position A. The deviation is noted as a displacement Dxy.

Figure 3:
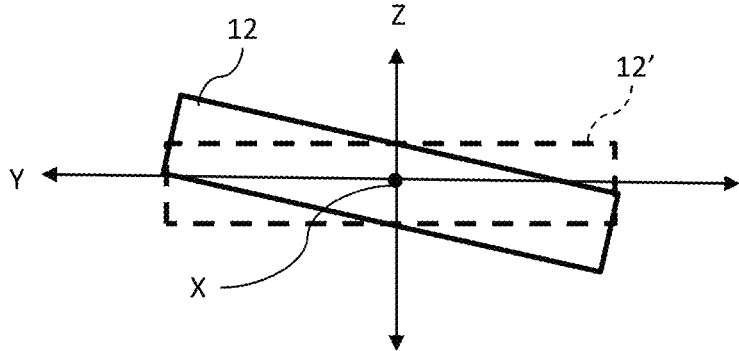
FIG. 3 is an illustration showing a front view of a patient bed.

In another example shown in FIG. 3, which is a view from the forward end of the patient bed pallet 12 (refer to FIG. 4). The patient bed pallet 12' rendered in dashed line represent the desired position of the patient bed pallet that does not roll as it moves from Position A to Position B. In this illustrated example, the patient bed pallet 12 has rolled and resulted in a rotational deviation of the pallet 12 from the desired position as it moved from Position B from Position A.

Any such deviation in the position or orientation of the patient bed pallet 12 means that the body of the patient lying on the patient bed will appear to be moving in non-axial direction as the patient bed is moving from Position A to Position B. This will result in unwanted defects in the image reconstructed from the scan data and affect the quality of the reconstructed image.

The deviation of the patient bed pallet's movement from the desired ideal orientation can be the result of structural imperfections in the floor that is supporting the scanner assembly caused by settling of the floor over time after the initial installation and setup of the scanner system. Although rarely seen, the deviation can also be the result of deterioration of the structural integrity of the scanner assembly. Regardless of the cause, such deviation in the orientation of the patient bed pallet during its movement needs to be corrected to maintain the quality of the image reconstructed from the scanning data.

However, waiting until the deterioration of the quality of the reconstructed image is noticeable to adjust the patient bed pallet assembly can result in many medical image scans conducted in the interim to be sub-optimal in quality.

The present disclosure provides a solution by providing at least one multi-axis motion sensor 30 at or near the leading edge 12T of the patient bed pallet 12. The multi-axis motion sensor 30 can detect the displacements Dz and/or Dxy of the patient bed pallet in real-time as they occur and generate an output signal that includes information on the direction and amplitude of the displacement. Examples of such multi-axis sensor are 3-axis, 6-axis, and 9-axis motion sensors. Such sensors can detect the angle it is tilted at with respect to the earth by measuring the amount of acceleration due to gravity. By sensing the amount of dynamic acceleration, such accelerometer can determine how fast and in what direction the device is moving.

The result is a patient bed pallet 12 for a medical image scanner system 100 comprising: at least one multi-axis motion sensor 30 provided on the patient bed pallet 12, wherein the patient bed pallet 12 is configured to move in a linear path, wherein the multi-axis motion sensor 30 monitors the movement of the patient bed pallet 12 and detects any deviation in the patient bed pallet's orientation from a predetermined desired orientation.

In some embodiments, the predetermined desired orientation is horizontal.

Also provided is a medical image scanner 100 comprising: a detector ring 50 having a patient tunnel 59; a patient bed pallet 12 that is configured to move within the patient tunnel 59; and at least one multi-axis motion sensor 30 provided on the patient bed pallet 12, wherein the multi-axis motion sensor 30 monitors the movement of the patient bed pallet 12 when the patient bed pellet is moving within the patient tunnel 59 and detects any deviation (e.g. Dz, and/or Dxy) in the patient bed pallet's orientation from a predetermined desired orientation.

In some embodiments of the medical image scanner 100, the patient bed pallet 12 is configured to move within the patient tunnel in a linear path. The patient tunnel 59 has a defined longitudinal axis L and the patient bed pallet is configured to move within the patient tunnel 59 parallel to the longitudinal axis L. The predetermined desired orientation is parallel to the longitudinal axis L. In some embodiments, the longitudinal axis L is horizontal. In some embodiments, the predetermined desired orientation is parallel to the longitudinal axis L.

This set up allows real-time tracking of the patient bed pallet 12 orientation during its motion whether it be during an actual scanning session of a patient or during a system set up or quality control runs and detect any errors in the patient bed pellet's orientation. The real-time tracking can provide many advantageous features to the medical image scanner systems. For example, the real-time tracking data can be used to discard patient scan data when the deviation in the patient bed motion is outside an acceptable range. The real-time tracking data can be used to incorporate motion information in the histogramming of the PET or SPECT scan data and/or image reconstruction to compensate for the detected motion similar to the way CBM PET scanner systems compensate for the continuous bed motion.

Depending on the condition of the scanner's environment, such as the floor of the room, mechanical and structural condition of the moving mechanism that moves the patient bed pallet 12, etc., the orientation of the patient bed pallet at different patient bed location can deviate from the intended orientation over time. Whether the imaging scanner is used in single bed position scan, S & S scan, or CBM scan applications, because the patient bed pallet 12 can be at different physical location for different scans, each of these scanning modes can be negatively affected by such deviations in the patient bed pallet orientation. Therefore, the patient bed pallet orientation monitoring solution provided herein can be useful in single bed position scan, S & S scan, and CBM scan applications for detecting any deviation in the orientation of the patient bed pallet from the desired orientation set during installation of the scanners. Additionally, because the FOV of the complementary scans in PET/CT and SPECT/CT, for example, are not in the same imaging plane, the orientation of the patient bed pallet 12 may not match the spatial location calibration that was done between the PET and CT or SPECT and CT if the scanners' environmental factors deteriorate over time. Thus, the solution provided herein can be useful in such applications.

The real-time tracking data can also be used as a CBM quality control to verify that the patient bed pallet is moving in the intended path for the CBM mode.

These improved features of a medical image scanner system can ensure proper alignment of the patient bed and result in better customer confidence. The real-time tracking feature can also be useful during the initial medical image scanner system installation and set up in verifying that the scanner assembly is installed properly.

In some embodiments, the patient bed movement information from the at least one multi-axis motion sensor 30 can be retrieved by the scanner system controller on a periodic basis and a flag can be issued should the patient bed move outside of an acceptable range for deviation from the desired orientation. For example, this error can be flagged to the hardware service personnel for a repair.

In some embodiments of a PET, PET/CT, SPECT, SPECT/CT, CT, and MRI scanner systems, the data from the at least one multi-axis motion sensor 30 can be captured in the listmode data files for use in data processing and reconstruction to compensate for the detected deviation in the orientation of the patient bed pallet which in turn represents a deviation in the orientation and position of the scanned patient body. In many current PET, PET/CT, SPECT, and SPECT/CT scanner systems, the patient bed position information from horizontal and vertical bed encoders is inserted into the listmode data file at a fixed time period. In the embodiments of the improved scanner systems disclosed herein, the data from the at least one multi-axis motion sensor 30 is added to the listmode data file as an extension, without the current expectation that the patient orientation and location is fully defined by the horizontal and vertical bed encoders.

The patient bed pallet motion tracking disclosed herein can be applied to various medical imaging systems such as MRI, SPECT, PET, PET/CT, CT, etc.

It will be understood that the foregoing description is of exemplary embodiments of this invention, and that the invention is not limited to the specific forms shown. Modifications may be made in the design and arrangement of the elements without departing from the scope of the invention.

We claim:

1. A medical image scanner comprising:
a detector ring having a patient tunnel;
a patient bed pallet that is configured to move in a path within the patient tunnel; and
at least one multi-axis motion sensor provided on the patient bed pallet, wherein the multi-axis motion sensor monitors the movement of the patient bed pallet when the patient bed pallet is moving in the path within the patient tunnel and detects any deviation in the patient bed pallet's orientation from a predetermined desired orientation at any selected location along the path by measuring any pitch displacement Dz and yaw displacement Dxy of the patient bed pallet.

2. The medical image scanner of claim 1, wherein the patient bed pallet is configured to move within the patient tunnel in a linear path.

3. The medical image scanner of claim 1, wherein the at least one multi-axis motion sensor is a 3-axis motion sensor, a 6-axis motion sensor, or a 9-axis motion sensor.

4. The medical image scanner of claim 1, wherein the patient tunnel has a defined longitudinal axis and the patient bed pallet is configured to move within the patient tunnel parallel to the longitudinal axis.

5. The medical image scanner of claim 4, wherein the predetermined desired orientation is parallel to the longitudinal axis.

6. The medical image scanner of claim 4, wherein the longitudinal axis is horizontal.

7. The medical image scanner of claim 6, wherein the predetermined desired orientation is parallel to the longitudinal axis.

8. The medical image scanner of claim 1, wherein the medical image scanner is one of a PET scanner, PET/CT scanner, SPECT scanner, SPECT/CT scanner, CT scanner, and MRI scanner.

9. A patient bed pallet for a medical image scanner system comprising:
at least one multi-axis motion sensor provided on the patient bed pallet,
wherein the patient bed pallet is configured to move in a predetermined path, wherein the multi-axis motion sensor monitors the movement of the patient bed pallet when the patient bed pallet is moving in the predetermined path and detects any deviation in the patient bed pallet's orientation from a predetermined desired orientation at any selected location along the predetermined path by measuring any pitch displacement Dz and yaw displacement Dxy of the patient bed pallet.

10. The patient bed pallet of claim 9, wherein the predetermined path is a linear path.

11. The patient bed pallet of claim 9, wherein the at least one multi-axis motion sensor is a 3-axis motion sensor, a 6-axis motion sensor, or a 9-axis motion sensor.

12. The patient bed pallet of claim 9, wherein the predetermined desired orientation is horizontal.

* * * * *